United States Patent
Griffin et al.

(10) Patent No.: US 7,670,302 B2
(45) Date of Patent: Mar. 2, 2010

(54) SUPER ELASTIC GUIDEWIRE WITH SHAPE RETENTION TIP

(75) Inventors: Stephen Griffin, Sunnyvale, CA (US); Ronald A. Saharjian, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/025,668

(22) Filed: Dec. 18, 2001

(65) Prior Publication Data

US 2003/0114777 A1 Jun. 19, 2003

(51) Int. Cl.
*A61M 25/00* (2006.01)
(52) U.S. Cl. .................................... 600/585
(58) Field of Classification Search ............... 600/433, 600/434, 435, 585; 604/164.13, 170.01, 604/171
See application file for complete search history.

(56) References Cited

U.S. PATENT DOCUMENTS

| | | | |
|---|---|---|---|
| 3,467,101 A | 9/1969 | Fogarty et al. | |
| 4,385,635 A | 5/1983 | Ruiz | |
| 4,430,083 A | 2/1984 | Ganz et al. | |
| 4,547,193 A | 10/1985 | Rydell | |
| 4,569,347 A | 2/1986 | Frisbie | |
| 4,690,175 A | 9/1987 | Ouchi et al. | |
| 4,801,297 A | 1/1989 | Mueller | |
| 4,925,445 A | 5/1990 | Sakamoto et al. | |
| 4,960,410 A | 10/1990 | Pinchuk | |
| 4,998,923 A | 3/1991 | Samson et al. | |
| 5,069,226 A | 12/1991 | Yamauchi et al. | |
| 5,095,915 A | 3/1992 | Engelson | |
| 5,114,402 A | 5/1992 | McCoy | |
| 5,180,376 A | 1/1993 | Fischell | |
| 5,213,111 A | 5/1993 | Cook et al. | |
| 5,364,357 A | 11/1994 | Aase | |
| 5,368,049 A * | 11/1994 | Raman et al. | 600/585 |
| 5,381,782 A | 1/1995 | DeLaRama et al. | |
| 5,409,015 A | 4/1995 | Palermo | |
| 5,437,288 A | 8/1995 | Schwartz et al. | |
| 5,443,455 A | 8/1995 | Hergenrother et al. | |
| 5,452,726 A | 9/1995 | Burmeister et al. | |
| 5,454,787 A | 10/1995 | Lundquist | |
| 5,456,665 A | 10/1995 | Postell et al. | |
| 5,458,605 A | 10/1995 | Klemm | |

(Continued)

FOREIGN PATENT DOCUMENTS

DE 4104092 8/1991

(Continued)

OTHER PUBLICATIONS

"contiguous." Dictionary.com Unabridged (v 1.1). Random House, Inc. Dec. 21, 2006. <Dictionary.com http://dictionary.reference.com/browse/contiguous>.*

*Primary Examiner*—Max Hindenburg
*Assistant Examiner*—Jonathan M Foreman
(74) *Attorney, Agent, or Firm*—Crompton, Seager & Tufte, LLC

(57) ABSTRACT

A guidewire having a super elastic core surrounded by a shape memory polymer jacket. The super elastic core wire permits the guidewire to be navigated through tortuous vasculature without undergoing plastic deformation, and the shape memory polymer jacket permits the guidewire to be shaped by the physician.

14 Claims, 2 Drawing Sheets

U.S. PATENT DOCUMENTS

| | | | |
|---|---|---|---|
| 5,507,766 A | 4/1996 | Kugo et al. | |
| 5,531,719 A | 7/1996 | Takahashi | |
| 5,542,434 A | 8/1996 | Imran et al. | |
| 5,546,958 A | 8/1996 | Thorud et al. | |
| 5,569,200 A | 10/1996 | Umeno et al. | |
| 5,573,520 A | 11/1996 | Schwartz et al. | |
| 5,596,996 A | 1/1997 | Johanson et al. | |
| 5,636,642 A | 6/1997 | Palermo | |
| 5,662,621 A * | 9/1997 | Lafontaine | 604/528 |
| 5,716,410 A | 2/1998 | Wang et al. | |
| 5,722,424 A | 3/1998 | Engelson | |
| 5,741,429 A | 4/1998 | Donadio, III et al. | |
| 5,749,837 A | 5/1998 | Palermo | |
| 5,750,206 A | 5/1998 | Hergenrother et al. | |
| 5,762,630 A * | 6/1998 | Bley et al. | 604/164.01 |
| 5,769,796 A | 6/1998 | Palermo et al. | |
| 5,772,609 A * | 6/1998 | Nguyen et al. | 600/585 |
| 5,776,100 A | 7/1998 | Forman | |
| 5,780,807 A | 7/1998 | Saunders | |
| 5,782,809 A | 7/1998 | Umeno et al. | |
| 5,813,997 A | 9/1998 | Imran et al. | |
| 5,814,063 A | 9/1998 | Freitag | |
| 5,814,705 A | 9/1998 | Ward et al. | |
| 5,827,201 A | 10/1998 | Samson et al. | |
| 5,833,632 A | 11/1998 | Jacobsen et al. | |
| 5,836,303 A * | 11/1998 | Hurst et al. | 128/206.24 |
| 5,836,893 A | 11/1998 | Urick | |
| 5,843,031 A | 12/1998 | Hermann et al. | |
| 5,843,050 A | 12/1998 | Jones et al. | |
| 5,860,938 A | 1/1999 | Lafontaine et al. | |
| 5,916,178 A | 6/1999 | Noone et al. | |
| 5,921,956 A | 7/1999 | Grinberg et al. | |
| 5,938,623 A | 8/1999 | Quiachon et al. | |
| 5,944,701 A * | 8/1999 | Dubrul | 604/264 |
| 5,957,966 A * | 9/1999 | Schroeppel et al. | 607/122 |
| 5,964,714 A | 10/1999 | Lafontaine | |
| 5,984,878 A | 11/1999 | Engelson | |
| 6,001,068 A | 12/1999 | Uchino et al. | |
| 6,019,736 A | 2/2000 | Avellanet et al. | |
| 6,024,764 A * | 2/2000 | Schroeppel | 607/122 |
| 6,059,815 A * | 5/2000 | Lee et al. | 606/209 |
| 6,090,072 A | 7/2000 | Kratoska et al. | |
| 6,096,012 A | 8/2000 | Bogert et al. | |
| 6,139,510 A | 10/2000 | Palermo | |
| 6,146,339 A | 11/2000 | Biagtan et al. | |
| 6,156,842 A * | 12/2000 | Hoenig et al. | 324/318 |
| 6,160,084 A | 12/2000 | Langer et al. | |
| 6,168,604 B1 | 1/2001 | Cano | |
| 6,181,136 B1 * | 1/2001 | Choi et al. | 525/171 |
| 6,183,443 B1 | 2/2001 | Kratoska et al. | |
| 6,193,706 B1 | 2/2001 | Thorud et al. | |
| 6,485,458 B1 * | 11/2002 | Takahashi | 604/104 |
| 2001/0009980 A1 | 7/2001 | Richardson et al. | |
| 2002/0068968 A1 * | 6/2002 | Hupp | 623/1.15 |
| 2002/0165478 A1 * | 11/2002 | Gharib et al. | 604/8 |
| 2002/0183654 A1 * | 12/2002 | Zhou | 600/585 |

FOREIGN PATENT DOCUMENTS

| | | |
|---|---|---|
| EP | 0 063 859 A2 | 3/1982 |
| EP | 0 102 685 B1 | 5/1982 |
| EP | 0 411 118 A1 | 3/1988 |
| EP | 0 370 785 A1 | 11/1989 |
| EP | 0 437 795 B1 | 12/1990 |
| EP | 0 594 201 B1 | 10/1993 |
| EP | 0 608 853 A2 | 1/1994 |
| EP | 0 631 791 B1 | 6/1994 |
| EP | 0 688 576 B1 | 6/1995 |
| EP | 0 778 039 A1 | 12/1996 |
| FR | 2713492 | 6/1995 |
| JP | 03033809 A * | 2/1991 |
| JP | 8257128 | 10/1991 |
| WO | WO 93/04722 | 3/1993 |
| WO | WO 96/38193 | 12/1996 |
| WO | WO 99/11313 | 3/1999 |
| WO | WO 99/46109 A1 | 9/1999 |
| WO | WO 01/07499 A1 | 2/2001 |

* cited by examiner

SUPER ELASTIC GUIDEWIRE WITH SHAPE RETENTION TIP

FIELD OF THE INVENTION

The present invention generally relates to intravascular guidewires. More specifically, the present invention relates to intravascular guidewires utilizing super elastic materials.

BACKGROUND OF THE INVENTION

Intravascular guidewires are commonly used to navigate through a patient's vascular system for the diagnosis and treatment of a wide variety of vascular disorders. Guidewires conventionally utilize a stainless steel or nitinol (super elastic) core wire. Stainless steel core wires are advantageous because they are shapeable, but are disadvantageous because they may become deformed in tortuous vascular anatomy. Nitinol core wires are advantageous because they do not become deformed in tortuous vasculature, but are disadvantageous because they are not shapeable. Thus, there is a need for a guidewire that offers both advantages, namely a guidewire that is shapeable and that is not readily deformed in tortuous vasculature.

SUMMARY OF THE INVENTION

To address this need, the present invention provides several design alternatives. For example, in one embodiment, the present invention provides a guidewire having a super elastic core wire surrounded by a shape memory polymer jacket. The super elastic core wire permits the guidewire to be navigated through tortuous vasculature without undergoing plastic deformation, and the shape memory polymer jacket permits the guidewire to be shapeable.

DETAILED DESCRIPTION OF THE INVENTION

The following detailed description should be read with reference to the drawings in which similar elements in different drawings are numbered the same. The detailed description and the drawings, which are not necessarily to scale, depict illustrative embodiments and are not intended to limit the scope of the invention.

Figure 1:
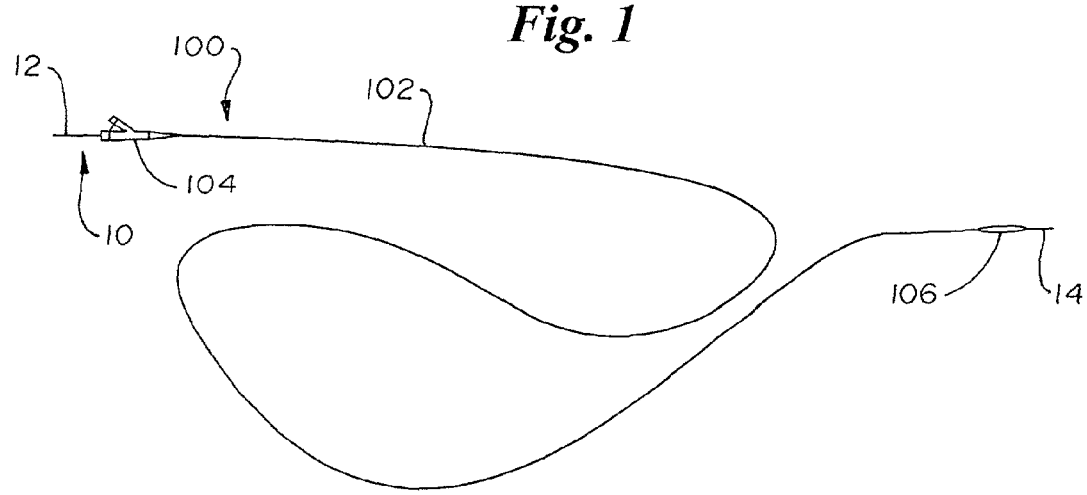
FIG. 1 is a plan view of a guidewire according to the present invention, in combination with a balloon catheter.

Refer now to FIG. 1 which illustrates a plan view of a guidewire 10 in combination with an intravascular device 100. In this particular example, the intravascular device 100 comprises a balloon catheter, but those skilled in the art will recognize that guidewires may be used alone or in combination with a wide variety of intravascular devices for coronary, peripheral and cerebral use, including balloon catheters, guide catheters, diagnostic catheters, micro-catheters, etc. For purposes of illustration only, intravascular device 100 is shown to be a balloon catheter 100 having an elongate shaft 102, a proximally disposed manifold 104, and a distally disposed inflatable balloon 106, all of which are conventional in the art. Guidewire 10 may extend through the entire length of the balloon catheter 100, and includes a proximal end 12 and a distal tip portion 14. The guidewire 10 may have a size (length and diameter) to navigate coronary, peripheral and/or cerebral vasculature, depending on the particular clinical application, and the distal tip portion 14 may be shaped to facilitate steering in such vascular anatomy.

Figure 2:
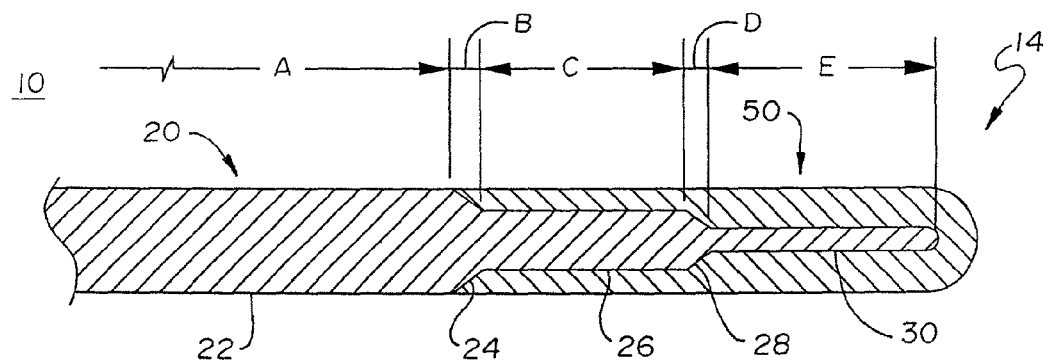
FIG. 2 is a foreshortened longitudinal cross-sectional view of a distal portion of a guidewire of the present invention, showing a polymer jacket surrounding a distal tip of a core wire.
Figure 3:
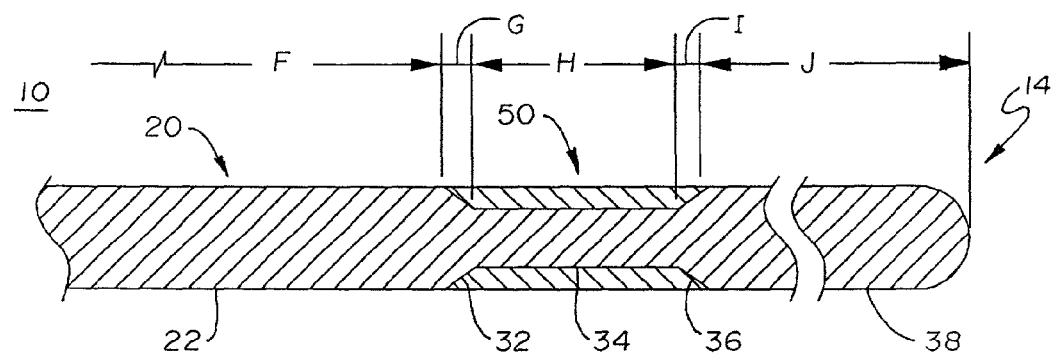
FIG. 3 is a foreshortened longitudinal cross-sectional view of a portion of a guidewire of the present invention, showing a polymer jacket surrounding a mid portion of a core wire.
Figure 4:
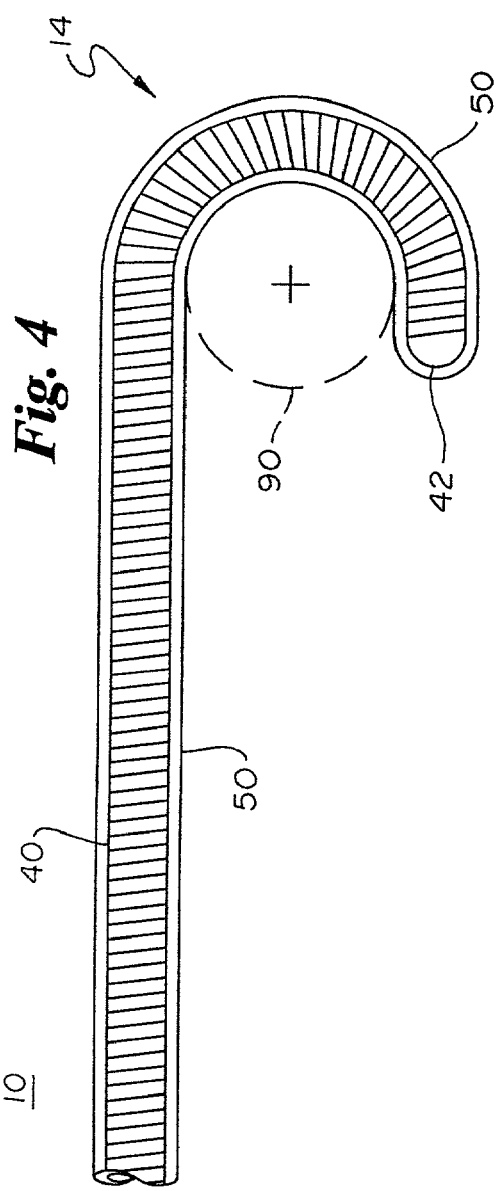
FIGS. 4 and 5 are side views of a distal tip portion of a guide wire showing a polymer jacket surrounding a distal portion of a spring tip and core wire, wherein the distal tip is deformed about a cylinder-shaped object.
Figure 5:
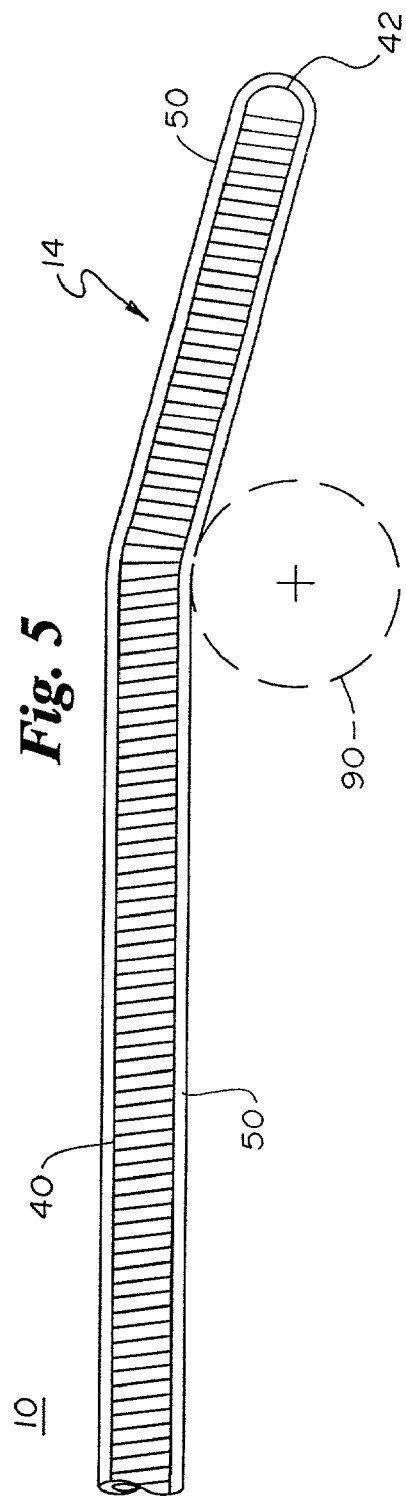

As seen in FIG. 2, the guidewire 10 may include a core wire 20 with a polymer jacket 50 surrounding a distal tip portion 14 thereof. Alternatively, the polymer jacket 50 may surround a mid portion of the guidewire 10 as shown in FIG. 3. As shown in FIGS. 4 and 5, a radiopaque coil 40 may surround a distal portion 14 of the core wire 20, with a distal weld 42 connecting the distal end of the coil 40 to the distal end of the core wire 20 (not visible in FIGS. 4 and 5). In this latter instance, the polymer jacket 50 may surround the core wire 20 and the radiopaque coil 40. As a further alternative, the polymer jacket 50 may surround an inner polymer jacket (not shown) disposed on the core wire 20, resulting in a multi-layered polymer jacket arrangement, with layer thicknesses that may vary, but preferably do not exceed the proximal profile of the guidewire. In all embodiments, the polymer jacket 50 may incorporate radiopaque filler.

In all embodiments illustrated, the polymer jacket 50 may surround the core wire 20 and/or radiopaque coil 40 to establish contact therebetween or to establish an annular space therebetween. In addition, the polymer jacket 50 may surround and encase the core wire 20 and/or radiopaque coil 40 to encase the distal tip 14 as shown in FIGS. 2, 4 and 5, or merely surround a portion thereof without encasing as shown in FIG. 3.

Core wire 20 may comprise a stainless steel metal or a super elastic metal such as nitinol (nickel titanium alloy) for purposes of navigating tortuous vasculature without causing plastic deformation thereof. Polymer jacket 50 may comprise a polymer and may have suitable dimensions and material characteristics that render the polymer jacket 50 more stiff than the distal tip portion 14 of the super elastic core wire 20 which it surrounds. As used herein, stiff or stiffness refers to the collective property defined by material characteristics and shape, as conventionally used in mechanical engineering design. In particular, the cross-sectional bending moment and the flexural modulus of the polymer jacket 50 may be selected such that when the tip 14 is deformed into a shape within the elastic limit of the super elastic core wire 20, and beyond the elastic limit of the polymer, the tip 14 substantially retains the shape, although some recoil may occur.

The polymer jacket 50 may comprise a shape memory polymer such as shape memory polyurethane available from Mitsubishi, polynorbornene polymers and copolymers (including blends with polyethylene and Kraton), polycaprolactone or (oligo)caprolactone copolymer, polymethylmethacylate, PLLA or PL/D LA copolymer, PLLA PGA copolymer, PMMA, cross-linked polyethylene, cross-linked polyisoprene, polycyclooctene, styrene-butadiene copolymer, or photocrosslinkable polymer including azo-dye, zwitterionic and other photochromic materials (as referenced in *Shape memory Materials*, Otsuka and Wayman, Cambridge University press, ©1998).

With a shape memory polymer, the distal tip 14, including polymer jacket 50, core wire 20, and/or radiopaque coil 40, may be deformed into the desired shape. By way of example, not limitation, the distal tip portion 14 may be deformed about a cylindrical object 90 to impart a J-tip shape as shown in FIG. 4, or a bent-L shape as shown in FIG. 5. Although only basic shapes are shown, it is contemplated that a wide variety of simple and complex shapes may be achieved with the present invention. While the desired shape is maintained, the polymer jacket 50 may be subjected to heat at a temperature at or above the glass transition temperature (or near the melt temperature) of the shape memory polymer, and subsequently cooled to a temperature below the glass transition temperature. Once cooled, the distal tip 14 may be released from the constrained shape. The glass transition temperature is preferably greater than the temperature of the environment where guidewire 10 will be used (i.e. the internal body temperature of a patient), so as to sustain the desired shape while guidewire 10 is used (e.g. navigated through a vessel lumen of a patient). In other words, the temperature of the environment where guidewire 10 will be used is lower than the glass transition temperature that will allow polymer jacket 50 to change shape.

After releasing the distal tip 14 from the constrained shape, the elastic forces of the super elastic core wire 20 work against the polymer jacket 50, biasing the shape of the distal tip back to the original (e.g., straight) configuration. However, the polymer jacket 50 has sufficient stiffness, by virtue of its size and its material properties, to substantially oppose, if not completely offset, the biasing force of the super elastic core wire 20. The biasing force of the core wire 20 may be reduced by reducing the size (e.g., diameter) thereof, and the opposing force of the polymer jacket 50 may be increased by increasing the size (cross-sectional area moment) and/or the flexural modulus thereof. Thus, by substantially opposing, if not completely offsetting, the biasing force of the super elastic core wire 20, the polymer jacket 50 substantially maintains the deformed shape, although some recoil may occur. To compensate for such recoil, the deformed shape may be exaggerated relative to the desired final shape.

The distal tip 14 may be re-shaped by re-deforming the distal tip 14 and exposing the polymer jacket 50 to heat at a temperature at or above the glass transition temperature (or near the melt temperature) of the shape memory polymer, and subsequently cooled to a temperature below the glass transition temperature. The original (e.g., straight) configuration of the distal tip 14 may be recaptured by exposing the polymer jacket 50 to heat at a temperature at or above the transformation temperature of the shape memory polymer, followed by cooling. The distal tip 14 may be repeatedly shaped without compromising shapeability or guidewire performance.

The polymer jacket 50 may surround the distal tip portion 14 as shown in FIG. 2 or a mid portion of the core wire 20 as shown in FIG. 3. To accommodate the polymer jacket 50 and to provide a uniform outer profile, the core wire 20 may be ground to have a single taper or a series of tapers as shown in FIG. 2 or ground to define a recess as shown in FIG. 3.

In FIG. 2, the distal portion 14 of the core wire 20 includes a series of tapers to accommodate the polymer jacket 50 and to provide a gradual reduction in stiffness toward the distal end thereof. For example, the core wire 20 may have a proximal uniform diameter portion 22 having a diameter of about 0.007 to 0.038 inches and a length "A" of about 100 to 260 cm, a mid uniform diameter portion 26 having a diameter of about 0.003 to 0.010 inches and a length "C" of about 5 to 30 cm, and a distal uniform diameter portion 30 having a diameter of about 0.0015 to 0.005 inches and a length "E" of about 5 to 30 cm. Alternatively, distal portion 30 may comprise a flat ribbon having a thickness of 0.0015 to 0.005 inches. The core wire 20 may also include tapered portions 24/28 between the uniform diameter portions 22/26/30, having tapering diameters and lengths "B" and "D" of about 0.1 to 10 cm to provide a smooth transition between the uniform diameter portions 22/26/30. As an alternative, the core wire 20 may have a continuous taper terminating in a radiopaque tip, and covered by the polymer jacket 50.

In FIG. 3, a mid portion (i.e., a portion that is proximal of the distal end and distal of the proximal end) of the core wire 20 is provided with an optional recess having a uniform diameter portion 34 and two tapered portions 32/36. The position of the recess 34 and thus the position of the polymer jacket 50 in this embodiment is dictated by the length "F" of the proximal uniform diameter portion 22 and the length "J" of the distal uniform diameter portion 38. The length "H" of the recess portion 34 may be selected depending on the desired shapeable length of the core wire 20. The lengths "G" and "I" of the tapered portion 32/36 may be the same or similar to that of tapered portions 24/28 described previously.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular guidewire selectively shapeable by a user and configured for navigation through a vessel lumen of a patient, the guidewire comprising:

an elongate core wire comprising a constant diameter portion and a tapered portion extending distally from the constant diameter portion to a distal end of the core wire, at least the tapered portion formed of a super elastic nickel titanium alloy which is not independently shapeable by forces normally subjected to during a medical procedure; and a polymer jacket comprising a shape memory polymer attached to and surrounding the tapered portion of the core wire formed of a super elastic nickel titanium alloy, the polymer jacket having a length extending proximally from the distal end of the core wire to at least the constant diameter portion, wherein the polymer jacket is in continuous contact with the core wire throughout a majority of the length of the polymer jacket, the polymer jacket being more stiff than the portion of the core wire formed of a super elastic nickel titanium alloy which it surrounds;

wherein the tapered portion of the core wire surrounded by the polymer jacket is bent into a curved shape, wherein the polymer jacket overcomes biasing forces imposed by the elongate core wire which tend to straighten the tapered portion of the core wire from the curved shape such that the stiffness of the polymer jacket retains the tapered portion of the elongate core wire in the curved shape in the vessel lumen of the patient;

wherein the shape memory polymer is one from a subset of polymers which are characterized by their responsiveness to heating at or above a glass transition temperature of the shape memory polymer in order to independently transform the shape memory polymer between a first shape and a second shape;

wherein the glass transition temperature of the shape memory polymer is greater than the body temperature of the patient such that the curved shape imparted in the elongate core wire is sustained when the guidewire is navigated through the vessel lumen of the patient.

2. An intravascular guidewire as in claim 1, wherein the shape memory polymer comprises shape memory polyurethane.

3. An intravascular guidewire as in claim 1, wherein the shape memory polymer comprises shape memory polynorbornene or copolymers or blends thereof.

4. An intravascular guidewire as in claim 1, wherein the shape memory polymer comprises shape memory polycaprolactone or (oligo)caprolactone copolymer.

5. An intravascular guidewire as in claim 1, wherein the shape memory polymer comprises shape memory polymethylmethacylate.

6. An intravascular guidewire as in claim 1, wherein the shape memory polymer comprises shape memory PLLA copolymer.

7. An intravascular guidewire as in claim 1, wherein the shape memory polymer comprises shape memory PLLA PGA copolymer.

8. An intravascular guidewire as in claim 1, wherein the shape memory polymer comprises shape memory PL/D LA copolymer.

9. An intravascular guidewire as in claim 1, wherein the shape memory polymer comprises shape memory PMMA copolymer.

10. An intravascular guidewire as in claim 1, wherein the shape memory polymer comprises shape memory cross-linked polyethylene.

11. An intravascular guidewire as in claim 1, wherein the shape memory polymer comprises shape memory cross-linked polyisoprene.

12. An intravascular guidewire as in claim 1, wherein the shape memory polymer comprises shape memory styrene-butadiene copolymer.

13. An intravascular guidewire as in claim 1, wherein the shape memory polymer comprises a photocrosslinkable polymer.

14. An intravascular guidewire selectively shapeable by a user and configured for navigation through a vessel lumen of a patient, the guidewire comprising:
- a core wire having a constant diameter portion and a tapered portion extending distally from the constant diameter portion to a distal end of the core wire, the tapered portion formed of a super elastic nickel titanium alloy; and
- a polymer jacket having a length, the polymer jacket attached to and surrounding the entire tapered portion from the distal end to the constant diameter portion of the core wire such that the polymer jacket is in continuous contact with the core wire throughout a majority of the length of the polymer jacket, the polymer jacket being more stiff than the portion of the core wire which it surrounds;
- wherein the tapered portion of the core wire surrounded by the polymer jacket is bent into a curved shape, wherein the polymer jacket overcomes biasing forces imposed by the tapered portion of the core wire which tend to straighten the tapered portion of the core wire from the curved shape such that the stiffness of the polymer jacket retains the tapered portion of the elongate core wire in the curved shape in the vessel lumen of the patient;
- wherein the polymer jacket comprises a shape memory polymer so characterized by its ability to independently transform to an alternate shape as a result of being subjected to heating at or above a glass transition temperature of the shape memory polymer;
- wherein the glass transition temperature of the shape memory polymer is chosen such that the curved shape imparted in the elongate core wire is sustained when the guidewire is navigated through the vessel lumen of the patient.

* * * * *

UNITED STATES PATENT AND TRADEMARK OFFICE
CERTIFICATE OF CORRECTION

| | | |
|---|---|---|
| PATENT NO. | : 7,670,302 B2 | Page 1 of 1 |
| APPLICATION NO. | : 10/025668 | |
| DATED | : March 2, 2010 | |
| INVENTOR(S) | : Stephen Griffin et al. | |

It is certified that error appears in the above-identified patent and that said Letters Patent is hereby corrected as shown below:

Title Page, Item (75)
Inventors: delete "Saharjian" and insert therefor -- Sahatjian --.

Signed and Sealed this
First Day of February, 2011

David J. Kappos
*Director of the United States Patent and Trademark Office*